(12) United States Patent
Nygren et al.

(10) Patent No.: US 11,608,485 B2
(45) Date of Patent: Mar. 21, 2023

(54) POWER CONVERTER FOR A BIOELECTROCHEMICAL SYSTEM

(71) Applicant: Solar Foods Oy, Lappeenranta (FI)

(72) Inventors: Lauri Nygren, Lappeenranta (FI); Andrey Lana, Lappeenranta (FI); Jero Ahola, Lappeenranta (FI); Vesa Ruuskanen, Lappeenranta (FI); Juha-Pekka Pitkänen, Lappeenranta (FI)

(73) Assignee: Solar Foods Oy, Lappeenranta (FI)

( * ) Notice: Subject to any disclaimer, the term of this patent is extended or adjusted under 35 U.S.C. 154(b) by 392 days.

(21) Appl. No.: 17/047,876

(22) PCT Filed: Apr. 2, 2019

(86) PCT No.: PCT/FI2019/050265
§ 371 (c)(1),
(2) Date: Oct. 15, 2020

(87) PCT Pub. No.: WO2019/202202
PCT Pub. Date: Oct. 24, 2019

(65) Prior Publication Data
US 2021/0179996 A1     Jun. 17, 2021

(30) Foreign Application Priority Data

Apr. 16, 2018   (FI) ..................... 20185360

(51) Int. Cl.
*H02M 7/217*   (2006.01)
*H02M 3/335*   (2006.01)
(Continued)

(52) U.S. Cl.
CPC .............. *C12M 35/02* (2013.01); *C25B 15/02* (2013.01); *H02M 1/00* (2013.01);
(Continued)

(58) Field of Classification Search
CPC ...... H02M 3/00; H02M 3/335; H02M 3/3353; H02M 3/33569; H02M 3/33571;
(Continued)

(56) References Cited

U.S. PATENT DOCUMENTS 9,209,699 B1   12/2015  Wu
2006/0114642 A1*  6/2006  Liu ....................... H02J 3/1892
361/500

(Continued)

FOREIGN PATENT DOCUMENTS

JP     S57156194 U    10/1982
JP     H02110951 U     9/1995
(Continued)

OTHER PUBLICATIONS

Finnish Patent and Registration Office, Search Report, Application No. 20185360, dated Dec. 4, 2018, 2 Pages.
(Continued)

*Primary Examiner* — Thienvu V Tran
*Assistant Examiner* — Shahzeb K Ahmad
(74) *Attorney, Agent, or Firm* — Ziegler IP Law Group LLC

(57) ABSTRACT

A power converter for a bioelectrochemical system includes first converters each including a direct current terminal for supplying electric current via electrodes of the bioelectrochemical system, and a second converter for supplying energy to the first converters from an external electric power grid. Each first converter includes an electric element for receiving energy from the second converter and a circuitry for converting voltage of the electric element into electrolysis voltage suitable for the bioelectrochemical system. The electric element can be a secondary winding of a transformer or a direct voltage energy storage. Each first converter is galvanically isolated from the other first converters at least (Continued)

when the first mentioned first converter supplies energy to the bioelectrochemical system. Thus, each first converter drives its own electrode pair without disturbing the other first converters.

9 Claims, 3 Drawing Sheets

(51) Int. Cl.
*C12M 1/42* (2006.01)
*C25B 15/02* (2021.01)
*H02M 1/00* (2006.01)
C25B 1/04 (2021.01)
H02M 3/00 (2006.01)
H02M 7/04 (2006.01)
H02M 7/12 (2006.01)

(52) U.S. Cl.
CPC ....... *H02M 3/33561* (2013.01); *H02M 7/217* (2013.01); *C25B 1/04* (2013.01); *H02M 1/0074* (2021.05); *H02M 3/00* (2013.01); *H02M 7/04* (2013.01); *H02M 7/12* (2013.01)

(58) Field of Classification Search
CPC ......... H02M 3/33573; H02M 3/33561; H02M 3/33576; H02M 7/04; H02M 7/12; H02M 7/125; H02M 7/155; H02M 7/21; H02M 7/217; H02M 7/219; H02M 1/00; H02M 1/0074; C12M 35/02; C12M 21/00; C25B 15/02; C25B 1/04; Y02E 60/36
See application file for complete search history.

(56) References Cited

U.S. PATENT DOCUMENTS

| | | |
|---|---|---|
| 2009/0309598 A1 | 12/2009 | Zhu et al. |
| 2010/0026095 A1* | 2/2010 | Phadke ................ H02M 3/285 |
| | | 307/31 |
| 2011/0315560 A1 | 12/2011 | Rabaey et al. |
| 2012/0100590 A1 | 4/2012 | Tartakovsky et al. |
| 2012/0199472 A1 | 8/2012 | Curfew |
| 2014/0062396 A1 | 3/2014 | Reddy |
| 2015/0194905 A1* | 7/2015 | White ................ H02M 7/2173 |
| | | 363/126 |
| 2018/0217370 A1* | 8/2018 | Malone ................ G02B 26/005 |
| 2018/0291516 A1* | 10/2018 | Nakao ........................ C25B 1/55 |

FOREIGN PATENT DOCUMENTS

| | | |
|---|---|---|
| JP | 2002101664 A | 4/2002 |
| JP | 2012512326 A | 5/2012 |
| WO | 2010068994 A1 | 6/2010 |
| WO | 2011000084 A1 | 1/2011 |

OTHER PUBLICATIONS

PCT, International Search Report, Application No. PCT/FI2019/050265, dated Jun. 26, 2019, 10 Pages.
Ruuskanen et al, "Design and implementation of a power-hardware-in-loop simulator for water electrolysis emulation", Renewable Energy, vol. 119, pp. 106-115, XP085333137, ISSN: 0960-1481, DOI: 10.1016/J. RENENE.2017.11.088, Dec. 1, 2017, 10 pages.
Japan Patent Office, Notification of Ground of Rejection, Application No. 2020-558477, dated Sep. 8, 2022, 2 pages.

* cited by examiner

POWER CONVERTER FOR A BIOELECTROCHEMICAL SYSTEM

FIELD OF THE DISCLOSURE

The disclosure relates to a power converter for driving electrolysis in cultivation medium of a bioelectrochemical system so as to split water into hydrogen and oxygen. Furthermore, the disclosure relates to a bioelectrochemical system comprising a bioreactor chamber and a power converter for driving electrolysis in the bioreactor chamber.

BACKGROUND

Hydrogen-oxidizing bacteria, e.g. chemolithoautotrophic bacteria, are capable of growing autotrophically by using hydrogen as an energy source to assimilate carbon dioxide into their biomass. This makes possible the conversion of carbon dioxide, water, and nutrients into bacterial biomass and/or other bioproducts, such as e.g. bioplastics and biofuels. A bioelectrochemical system for cultivating hydrogen-oxidizing bacteria comprises typically a bioreactor chamber for containing the hydrogen-oxidizing bacteria and suitable cultivation medium. Hydrogen can be supplied to the bioreactor chamber from an external source, but a problem related to this approach is low gas-to-liquid mass transfer of hydrogen. To increase the dissolution rate of hydrogen into the cultivation medium, hydrogen partial pressure in a bioreactor chamber headspace can be increased. This may however increase a danger of explosion, since hydrogen is flammable e.g. with air at volumetric concentrations ranging from 4 to 74.5% in the atmospheric pressure.

Another method for providing hydrogen is in situ water electrolysis in a bioreactor chamber so as to split water into hydrogen and oxygen with the aid of electric current. The electric current is supplied to electrodes submerged into cultivation medium. With in situ water electrolysis, poor dissolution of hydrogen and oxygen is not an issue, since they are generated in the cultivation medium. This may also give some freedom in the bioreactor design. The minimum voltage required for water electrolysis, called reversible voltage, is 1.23 V. Without auxiliary heat, the minimum voltage required is higher, and dependent on electrolysis conditions, e.g. 1.43 V in the ambient conditions. The actual voltage required to drive water electrolysis is higher due to voltage losses caused by the impedance between electrodes.

The in situ water electrolysis of the kind described above is however not free from challenges. From an energy efficiency point of view, voltage driving the water electrolysis should be retained as low as possible. However, too low voltage may have inhibitory effects on growth of bacteria, since reactive oxygen species "ROS" having toxic effects on bacteria can be generated instead of splitting water into hydrogen and oxygen. The reactive oxygen species can be for example hydrogen peroxide, superoxide, and hydroxyl radicals. On the other hand, too high current can also inhibit the growth. One of the challenges is related to local electric current densities in the cultivation medium, and especially in the vicinity of the electrodes, when electric current for obtaining sufficient hydrogen generation is driven via the electrodes. High local maxima in the electric current density may be harmful to or at least disturb the cultivation process.

SUMMARY

The following presents a simplified summary in order to provide a basic understanding of some aspects of various embodiments. The summary is not an extensive overview of the disclosed embodiments. It is neither intended to identify key or critical elements of the disclosed embodiments nor to delineate the scope of the disclosed embodiments. The following summary merely presents some concepts in a simplified form as a prelude to a more detailed description of exemplifying embodiments.

In accordance with the disclosed embodiments, there is provided a new power converter for driving water electrolysis in cultivation medium of a bioelectrochemical system so as to split water into hydrogen and oxygen. A power converter according to the disclosed embodiments comprises:

two or more first converters each comprising a direct current terminal for supplying electric current via electrodes of the bioelectrochemical system, and a second converter for supplying energy to each of the first converters from an external electric power grid.

Each of the above-mentioned first converters comprises at least one electric element for receiving energy from the second converter and at least one circuitry for converting voltage of the electric element into electrolysis voltage suitable for the bioelectrochemical system. Each of the first converters is galvanically isolated from the other first converters when the first mentioned first converter is supplying energy to the bioelectrochemical system. The above-mentioned electric element for receiving energy from the second converter can be for example a secondary winding of a transformer whose primary winding is connected to the second converter. For another example, the electric element can be a direct voltage energy storage which is connected to the second converter when the first converter under consideration does not supply energy to the bioelectrochemical system and disconnected from the second converter when the first converter supplies energy to the bioelectrochemical system.

In accordance with the disclosed embodiments, there is provided also a new bioelectrochemical system for cultivating bacteria, e.g. chemolithoautotrophic bacteria, and/or other microbes. A bioelectrochemical system according to the disclosed embodiments comprises:

a bioreactor chamber for cultivating the bacteria and/or other microbes, electrodes for splitting water contained by the bioreactor chamber into hydrogen and oxygen by water electrolysis, and a power converter according to the disclosed embodiments and arranged to supply direct currents via the electrodes, each of the electrodes being connected to only one of the first converters of the power converter.

As the above-mentioned first converters are galvanically isolated from each other when driving the water electrolysis, unexpected and undesired routes for electric currents from one of the first converters to another do not occur. Therefore, each of the first converters is arranged to drive its own electrodes without disturbing the operation of other ones of the first converters.

As there are many electrode pairs, sufficient hydrogen generation can be achieved with lower local current densities than in a case where only one electrode pair is used. Furthermore, hydrogen concentration over the cultivation space can be more uniformly distributed than in a case where only one electrode pair is used. As the above-mentioned first converters are galvanically isolated from each other when driving the water electrolysis, it is possible to arrange individual control and diagnosis for each electrode pair to overcome possible problems caused by local differences in the cultivation medium.

A power converter according to the disclosed embodiments can be modular so that the power converter is adaptable to bioelectrochemical systems of various sizes by connecting an appropriate number of first converters to the second converter. It is also possible to use two or more second converters if needed. Thus, power converters according to some embodiments of the present disclosure can be assembled from converter units which are suitable for mass-production.

Various exemplifying and non-limiting embodiments are described in accompanied dependent claims.

Various exemplifying and non-limiting embodiments of the present disclosure both as to constructions and to methods of operation, together with additional objects and advantages thereof, will be best understood from the following description of specific exemplifying and non-limiting embodiments when read in conjunction with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF THE FIGURES

Exemplifying and non-limiting embodiments and their advantages are explained in greater detail below in the sense of examples and with reference to the accompanying drawings, in which.

DESCRIPTION OF THE EXEMPLIFYING EMBODIMENTS

The specific examples provided in the description given below should not be construed as limiting the scope and/or the applicability of the appended claims. Lists and groups of examples provided in the description given below are not exhaustive unless otherwise explicitly stated.

Figure 1:
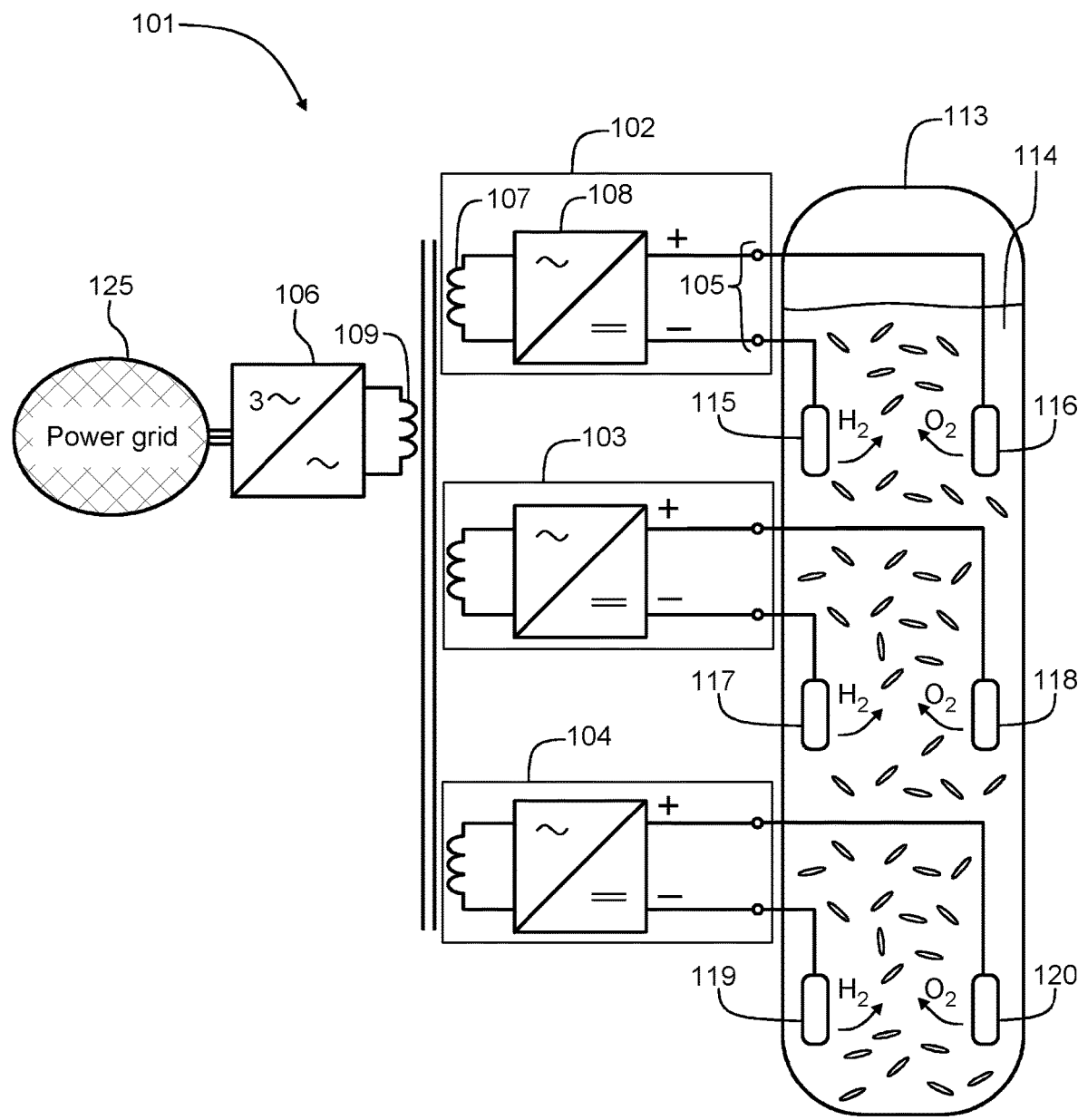
FIG. 1 shows a schematic illustration of bioelectrochemical system that comprises a power converter according to an exemplifying and non-limiting embodiment of the present disclosure.

FIG. 1 shows a schematic illustration of bioelectrochemical system that comprises a power converter 101 according to an exemplifying and non-limiting embodiment of the present disclosure. The bioelectrochemical system comprises a bioreactor chamber 113 for cultivating bacteria, e.g. chemolithoautotrophic bacteria, and/or other microbes. The bacteria and/or other microbes are cultivated in cultivation medium 114 that may comprise for example carbon dioxide, water, nutrients, and/or possible other substances needed in the cultivation process. In FIG. 1, the bacteria and/or other microbes are depicted with small ovals. The bioelectrochemical system comprises electrodes 115, 116, 117, 118, 119, and 120 for splitting water contained by the cultivation medium 114 into hydrogen $H_2$ and oxygen $O_2$ by water electrolysis. The bacteria and/or other microbes are capable of growing autotrophically by using the above-mentioned hydrogen as an energy source to assimilate carbon dioxide into their biomass. Thus, the carbon dioxide, water, and the nutrients can be converted into biomass and/or other bio-products, such as e.g. bioplastics and biofuels.

The power converter 101 comprises first converters 102, 103, and 104 each of which comprises a direct current "DC" terminal for supplying electric current via two of the electrodes of the bioelectrochemical system. In FIG. 1, the direct current terminal of the converter 102 is denoted with a reference 105. In the exemplifying case illustrated in FIG. 1, the converter 102 is connected to the electrodes 115 and 116, the converter 103 is connected to the electrodes 117 and 118, and the converter 104 is connected to the electrodes 119 and 120. The power converter 101 further comprises a second converter 106 for supplying energy to each of the converters 102-104 from an external electric power grid 125. Each of the converters 102-104 comprises an electric element for receiving energy from the converter 106. In FIG. 1, the electric element of the converter 102 is denoted with a reference 107. In the exemplifying case illustrated in FIG. 1, the electric element of each converter 102-104 is a secondary winding of a transformer whose primary winding 109 is connected to the converter 106. Each converter 102-104 comprises a circuitry for converting the voltage of the respective secondary winding into electrolysis direct voltage suitable for the bioelectrochemical system. In FIG. 1, the circuitry of the converter 102 is denoted with a reference 108. The circuitry 108 can be a controllable rectifier according to the prior art for converting the alternating voltage of the secondary winding into the electrolysis direct voltage. The electrolysis direct voltage can be for example in the range from 1.5 V to 3 V. The circuitry 108 may comprise for example an inductor-capacitor "LC" filter or an inductor-capacitor-inductor "LCL" filter for smoothing the electrolysis direct voltage. As each of the converters 102-104 has its own secondary winding as illustrated in FIG. 1, the converters 102-104 are galvanically isolated from each other. Therefore, unexpected and undesired routes for electric currents from one of the converters 102-104 to another do not occur and thereby each of the converters 102-104 is arranged to drive its own electrodes without disturbing the operation of other ones of the converters 102-104.

Figure 2:
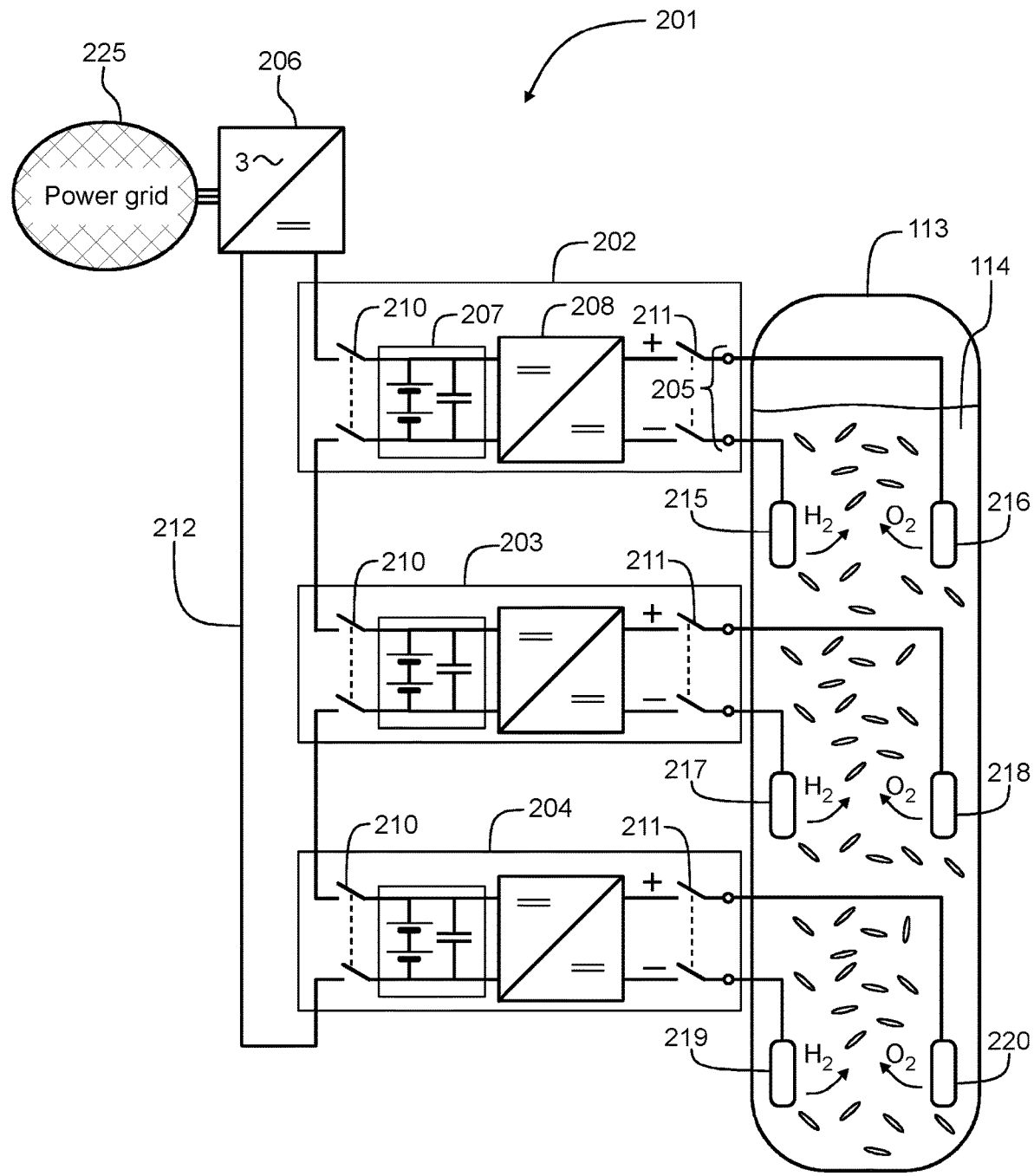
FIG. 2 shows a schematic illustration of a power converter according to an exemplifying and non-limiting embodiment of the present disclosure.

FIG. 2 shows a schematic illustration of a power converter 201 according to an exemplifying and non-limiting embodiment of the present disclosure. The power converter 201 comprises first converters 202, 203, and 204 each of which comprises a direct current "DC" terminal for supplying electric current via two of electrodes 215, 216, 217, 218, 219, and 220 of a bioelectrochemical system. In FIG. 2, the direct current terminal of the converter 202 is denoted with a reference 205. In the exemplifying case illustrated in FIG. 2, the converter 202 is connected to the electrodes 215 and 216, the converter 203 is connected to the electrodes 217 and 218, and the converter 204 is connected to the electrodes 219 and 220. The power converter 201 further comprises a second converter 206 for supplying energy to each of the converters 202-204 from an external electric power grid 225. Each of the converters 202-204 comprises an electric element for receiving energy from the converter 206. In FIG. 2, the electric element of the converter 202 is denoted with a reference 207. In the exemplifying case illustrated in FIG. 2, the electric element of each converter 202-204 is a direct voltage energy storage that comprises a parallel connection of a battery element and a capacitor element. Each converter 202-204 comprises a circuitry for converting the direct voltage of the respective direct voltage energy storage into electrolysis direct voltage suitable for the bioelectrochemical system. The electrolysis direct voltage can be for example in the range from 1.5 V to 3 V. In FIG. 2, the circuitry of the converter 202 is denoted with a reference 208. The circuitry 208 can be a controllable direct voltage-to-direct voltage "DC/DC" converter according to the prior art. The circuitry 208 may comprise for example an inductor-capacitor "LC" filter or an inductor-capacitor-inductor "LCL" filter for smoothing the electrolysis direct voltage.

Each of the converters 202-204 comprises a first switch system for disconnecting the direct voltage energy storage of the converter under consideration from a charging circuit 212 when the direct voltage energy storage is supplying energy to the bioelectrochemical system. In FIG. 2, the first switch systems of the converters 202-204 are denoted with a reference 210. Each of the converters 202-204 comprises a second switch system for disconnecting the direct voltage energy storage from the direct current terminal of the converter under consideration when the direct voltage energy storage is charged by the charging circuit 212. In FIG. 2, the second switch systems of the converters 202-204 are denoted with a reference 211. The operation is the bioelectrochemical system is periodic so that the power converter 201 is alternately in a charging state where the first switch systems 210 are conductive and the second switch systems 211 are non-conductive, and in an electrolysis state where the first switch systems 210 are non-conductive and the second switch systems 211 are conductive. In the exemplifying case illustrated in FIG. 2, the direct voltage energy storages of the converters 202-204 are series connected when being connected to the charging circuit 212. The series connection makes it possible to have higher output voltage of the converter 206 that can be a controllable a rectifier according to the prior art for converting the alternating voltage of the power grid 225 into direct voltage suitable for the series connection of the direct voltage energy storages. In conjunction with other embodiments of the present disclosure, it is possible that the direct voltage energy storages are parallel connected when being connected to the charging circuit, or the direct voltage energy storages are arranged to constitute parallel connected groups of series connected direct voltage energy storages or series connected groups of parallel connected direct voltage energy storages. A suitable connection arrangement is dependent on the electric properties of the converter 206 and the electric properties of the direct voltage energy storages.

As the converters 202-204 are galvanically isolated from each other when supplying energy via the electrodes 215-220, unexpected and undesired routes for electric currents from one of the converters 202-204 to another do not occur and thereby each of the converters 202-204 is arranged to drive its own electrodes without disturbing the operation of other ones of the converters 202-204.

Figure 3:
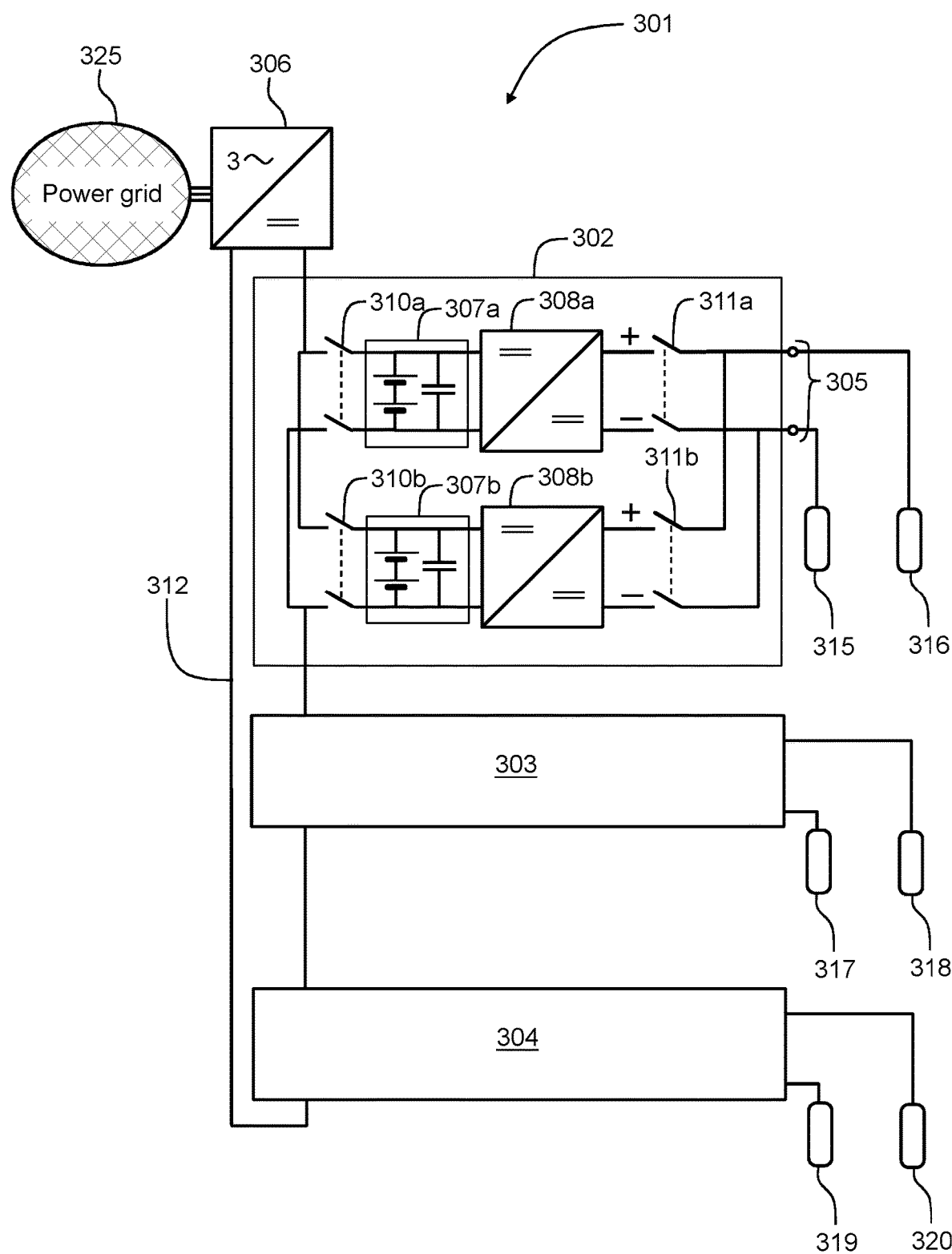
FIG. 3 shows a schematic illustration of a power converter according to an exemplifying and non-limiting embodiment of the present disclosure.

FIG. 3 shows a schematic illustration of a power converter 301 according to an exemplifying and non-limiting embodiment of the present disclosure. The power converter 301 comprises first converters 302, 303, and 304 each of which comprises a direct current "DC" terminal for supplying electric current via two of electrodes 315, 316, 317, 318, 319, and 320. In FIG. 3, the direct current terminal of the converter 302 is denoted with a reference 305. In the exemplifying case illustrated in FIG. 3, the converter 302 is connected to the electrodes 315 and 316, the converter 303 is connected to the electrodes 317 and 318, and the converter 304 is connected to the electrodes 319 and 320. The power converter 301 further comprises a second converter 306 for supplying energy to each of the converters 302-304 from an external electric power grid 325. FIG. 3 illustrates the functional elements of the converter 302, whereas the converters 303 and 304 are depicted as blocks. The converters 303 and 304 can be similar to the converter 302.

The converter 302 comprises two electric elements 307a and 307b for receiving energy from the converter 306. In the exemplifying case illustrated in FIG. 3, each of the electric elements 307a and 307b is a direct voltage energy storage that comprises a parallel connection of a battery element and a capacitor element. The converter 302 comprises two circuitries 308a and 308b for converting the direct voltage of the respective direct voltage energy storage into electrolysis direct voltage suitable for a bioelectrochemical system. The electrolysis direct voltage can be for example in the range from 1.5 V to 3 V. Each of the circuitries 308a and 308b can be a controllable direct voltage-to-direct voltage "DC/DC" converter according to the prior art. Each of the circuitries 308a and 308b may comprise for example an inductor-capacitor "LC" filter or an inductor-capacitor-inductor "LCL" filter for smoothing the electrolysis direct voltage.

The converter 302 comprises a first switch system that comprises switches 310a and 310b. The switch 310a is suitable for disconnecting the electric element 307a from a charging circuit 312 connected to the converter 306 when the electric element 307a is supplying energy via the electrodes 315 and 316. The switch 310b is suitable for disconnecting the electric element 307b from the charging circuit 312 when the electric element 307b is supplying energy via the electrodes 315 and 316. The converter 302 comprises a second switch system that comprises switches 311a and 311b. The switch 311a is suitable for disconnecting the circuitry 308a from the direct current terminal 305 when the electric element 307a is charged by the charging circuit 312. The switch 311b is suitable for disconnecting the circuitry 308b from the direct current terminal 305 when the electric element 307b is charged by the charging circuit 312. The converter 302 enables continuous water electrolysis so that the electric elements 307a and 307b and the circuitries 308a and 308b are arranged to drive the electrodes 315 and 316 in turns, i.e. one of the electric elements 307a and 307b is charged while the other one is supplying energy via the electrodes 315 and 316. The converter 306 can be a controllable a rectifier according to the prior art for converting the alternating voltage of the power grid 325 into direct voltage suitable for the electric elements being charged.

The specific examples provided in the description given above should not be construed as limiting the applicability and/or the interpretation of the appended claims. Lists and groups of examples provided in the description given above are not exhaustive unless otherwise explicitly stated.

What is claimed is:

1. A power converter for a bioelectrochemical system, the power converter comprising:
   two or more first converters each comprising a direct current terminal for supplying electric current via electrodes of the bioelectrochemical system, and
   a second converter for supplying energy to each of the first converters from an external electric power grid,
   wherein each of the first converters comprises at least one electric element for receiving energy from the second converter and at least one circuitry for converting voltage of the electric element into electrolysis voltage suitable for the bioelectrochemical system, wherein in that each of the first converters is galvanically isolated from other ones of the first converters when the first mentioned first converter is supplying energy to the bioelectrochemical system.

2. A power converter according to claim 1, wherein the electric element is a secondary winding of a transformer whose primary winding is connected to the second converter, and the circuitry is suitable for converting alternating voltage of the secondary winding into the electrolysis voltage.

3. A power converter according to claim 1, wherein the electric element is a direct voltage energy storage and each of the first converters comprises a first switch system for disconnecting the direct voltage energy storage from a charging circuit connected to the second converter when the direct voltage energy storage is supplying energy to the bioelectrochemical system and a second switch system for disconnecting the circuitry from the direct current terminal when the direct voltage energy storage is charged by the charging circuit.

4. A power converter according to claim 3, wherein the direct voltage energy storages of the first converters are series connected when being connected to the charging circuit.

5. A power converter according to claim 3, wherein the direct voltage energy storage comprises a battery element.

6. A power converter according to claim 3, wherein the direct voltage energy storage comprises a capacitor element.

7. A power converter according to claim 3, wherein each of the first converters comprises two direct voltage energy storages for receiving energy from the second converter and two circuitries for converting voltages of the two direct voltage energy storages into the electrolysis voltage, the first switch system being suitable for disconnecting each direct voltage energy storage from the charging circuit when the direct voltage energy storage under consideration is supplying energy to the bioelectrochemical system, and the second switch system being suitable for disconnecting each of the circuitries from the direct current terminal when the direct voltage energy storage connected to the circuitry under consideration is charged by the charging circuit.

8. A power converter according to claim 1, wherein each of the first converters is configured to control the electrolysis voltage to be in a range from 1.5 V to 3 V.

9. A bioelectrochemical system comprising:
a bioreactor chamber for cultivating microbes,
electrodes for splitting water contained by the bioreactor chamber into hydrogen and oxygen by water electrolysis, and
the power converter according to claim 1 and arranged to supply direct currents via the electrodes,
wherein each of the electrodes is connected to only one of the first converters of the power converter.

* * * * *